United States Patent
Sugaya et al.

(10) Patent No.: US 8,034,551 B2
(45) Date of Patent: Oct. 11, 2011

(54) METHOD, REAGENT AND KIT FOR MALARIA TESTING

(75) Inventors: Takeshi Sugaya, Ichikawa (JP); Eisei Noiri, Tokyo (JP); Yoshitsugu Matsumoto, Tokyo (JP)

(73) Assignees: The University of Tokyo, Tokyo (JP); Z Protein Laboratories, Inc., Moraga, CA (US)

( * ) Notice: Subject to any disclaimer, the term of this patent is extended or adjusted under 35 U.S.C. 154(b) by 24 days.

(21) Appl. No.: 12/405,060

(22) Filed: Mar. 16, 2009

(65) Prior Publication Data

US 2010/0068694 A1    Mar. 18, 2010

(30) Foreign Application Priority Data

Sep. 17, 2008   (JP) ................. 2008-238680

(51) Int. Cl.
*C12Q 1/00* (2006.01)
*G01N 33/53* (2006.01)
(52) U.S. Cl. ............................ 435/4; 435/7.1
(58) Field of Classification Search .................. None
See application file for complete search history.

(56) References Cited

U.S. PATENT DOCUMENTS

2007/0243560 A1* 10/2007 Yamanouchi et al. ......... 435/7.1

FOREIGN PATENT DOCUMENTS

JP         2006-304774        11/2006

OTHER PUBLICATIONS

Mutsuo Kobayashi et al. (2007 Annual Report on Summarized and Shared Individual Research , Principle Researcher Mutsuo Kobayashi, National Institute for Infectious Diseases, Department of Insect Medical Science reported Mar. 21, 2008).*

Mikolajczak et al. (international Journal of Parasitology vol. 37, pp. 483-489, 2007).*

Matsumoto et al., "Study on Malaria Aggravation Mechanism Using Animal Model—Elucidation of Pathogenic Mechanism of Severe Malaria such as Cerebral Malaria and Search for Biomarker as Indicator for Malaria Aggravation in particular," Ministry of Health, Labor and Welfare Grant-in-aid Scientific Research Emerging Reemerging Infectious Disease Research Project, Countermeasure Research on the Effective Prevention of Arthropod-borne Infectious Diseases (H18-Emergent-General-009), Mar. 21, 2008, pp. 269-274.

Mikolajczak et al., "L-FABP is a critical host factor for successful malaria liver stage development," International Journal for Parasitology, 37, 2007, pp. 483-489.

Kamijo et al., "Urinary liver-type fatty acid binding protein as a useful biomarker in chronic kidney disease," Molecular and Cellular Biochemistry, 284, 2006, pp. 175-182.

Negishi et al., "Renal L-type fatty acid-binding protein mediates the bezafibrate reduction of cisplati-induced acute kidney injury," Kidney International (original article) pp. 1-11, (http://www.kidney-international.org), 2008.

* cited by examiner

*Primary Examiner* — Gary Nickol
*Assistant Examiner* — Khatol Shahnan-Shah
(74) *Attorney, Agent, or Firm* — Knobbe Martens Olson & Bear LLP

(57) ABSTRACT

The present invention provides a method for malaria testing which enables testing for the presence of malaria infection and the extent of the infection in a convenient manner; and a reagent or kit which can be used in the method. The method for malaria testing according to the present invention includes the step of detecting a liver-type fatty acid binding protein present in urine collected from a subject animal. The extent of infection is determined to be higher when a larger amount of the liver-type fatty acid binding protein is present in a test sample.

9 Claims, 6 Drawing Sheets

METHOD, REAGENT AND KIT FOR MALARIA TESTING

This application is based on and claims the benefit of priority from Japanese Patent Application No. 2008-238680, filed on 17 Sep. 2008, the content of which is incorporated herein by reference.

BACKGROUND OF THE INVENTION

1. Field of the Invention

The present invention relates to a method for malaria testing, and a reagent or kit for testing, which can be used in the test method.

2. Related Art

Malaria is an infectious disease caused by infection with a malaria parasite, which is mediated by mosquitoes belonging to the genus *Anopheles*. Malaria parasites (*Plasmodium* spp.) are protozoa belonging to *Apicomplexa*, the members of which are obligate intracellular parasites, in other words, they can proliferate only in cells. Protozoan parasites exhibit comparatively high host specificity, and there are four kinds of malaria parasites that utilize humans as a definitive host, i.e., falciparum malaria parasites (*P. falciparum*), tertian malaria parasites (*P. vivax*), ovale malaria parasites (*P. ovale*), and quartan malaria parasites (*P. malariae*). Malaria caused by these four kinds of malaria parasites are referred to as falciparum malaria, tertian malaria, ovale malaria, quartan malaria, respectively.

It is estimated that the number of patients suffering from malaria is three to five hundred million per year throughout the world, with a death toll of 1.5 to 2.7 million per year. In addition, malaria parasites are indigenous to 100 or more countries predominantly in tropical and subtropical areas, and thus half the global population constantly faces the risk of malaria infection. Therefore, early detection and early treatment are important for preventing increases in the seriousness of the symptoms, and also for avoiding spreading of the infection.

As conventional methods for malaria testing (definitive diagnostic methods), which are widely carried out around the world, a Giemsa-stained thin-film smear preparation and a Giemsa-stained thick-film smear preparation of the blood collected from a subject are prepared, and the malaria-parasitized erythrocytes are then detected by microscopic observation of these preparations (see Non-patent Documents 1 and 2).

Furthermore, a test method in which a reagent for detecting malaria-parasitized erythrocytes is used which contains a DNA selective fluorescent dye, and a reagent for partial lysis of erythrocyte membrane capable of allowing the fluorescent dye to permeated into the erythrocyte while keeping the malaria parasites within the erythrocytes has also been proposed (see Patent Document 1). In this method, the blood collected from a subject and the reagent for detecting malaria-parasitized erythrocytes are mixed to prepare a measurement sample, and an excitation light is irradiated onto this measurement sample to identify the erythrocytes parasitized with malaria, based on the obtained scattering ray data and fluorescent data.

For the early detection and early treatment of malaria, or for disseminating the testing itself of malaria, it is necessary that the test method can be carried out in a convenient manner even in endemic areas of malaria. However, in the method described above including microscopic observation of a smear preparation, each of the steps of: production of a smear preparation; fixation; staining; and drying must be carried out, and thus complicated operations, as well as sufficient knowledge and experience are required. Therefore, training in microscopic observation has been performed for malaria testing as a national project in many endemic countries under instructions of the WHO.

Moreover, the method disclosed in Patent Document 1 necessitates complicated operations, and special apparatus such as a flow cytometer is required.

Accordingly, it cannot be said that any of these test methods could be readily carried out in endemic areas of malaria.

On the other hand, fatty acid binding proteins (FABPs) are known to be a group of proteins having a molecular weight of about 15 kD, are present in cytosol, and are able to bind to a fatty acid. The physiological functions of these proteins are considered to participate in the regulation of metabolic enzyme systems by transfer or accumulation of fatty acids within the cells, but the detailed physiological activities of these proteins have not been clarified yet. There have been known at least seven molecules of FABP such as liver-type (L-FABP), intestine-type (I-FABP), heart muscle-type (H-FABP), brain-type (B-FABP), cutaneous/epidermal-type (C-FABP/E-FABP), fat cell-type (aP2), peripheral neuron-type (myelin-P2), etc., and the primary structures thereof have been determined. All of these FABPs are able to bind to a fatty acid, and are recognized to have a region in which part of the sequence has been duly conserved, so that it is considered that they are members of a family evolved from the common ancestor genes. However, each FABP has a different primary structure as a whole, and shows a unique histologic distribution pattern. The nomenclature of FABP such as liver-type and intestine-type refers to the organ in which such FABP was found first, but does not mean that such an FABP is present exclusively in such organs.

In recent years, it has become known that L-FABP expression in hepatocytes relates to the liver stage development (exoerythrocytic development) of malaria parasites, and that down-regulation of L-FABP expression impairs malaria parasites growth, while overexpression of L-FABP promotes growth (see Non-patent Document 3).

However, in order to apply such findings to methods for malaria testing, L-FABP expression in hepatocytes have to be determined, and thus, they are not practical as test methods. In addition, although Non-patent Document 3 is a report concerning the exoerythrocytic development stage, no symptoms are present in the host during the exoerythrocytic development stage, which may be clinically referred to as a latent period. Therefore, it is also not practical as a test method in this respect. Furthermore, the extent of infection with malaria cannot be known from this test method, in contrast to the methods including microscopic observation of a smear preparation, and the like.

Accordingly, no convenient method for malaria testing which focuses on a L-FABP has been known so far.

Non-patent Document 1: Basic Malaria Microscopy, World Health Organization, 1991

Non-patent Document 2: Yukio Yoshida, "Human Parasitology Illustrated", Sixth edition, Nanzando Co., Ltd., 2002

Patent Document 1: Japanese Unexamined Patent Publication No. 2006-304774

Non-patent Document 3: Sebastian A. et al., L-FABP is a Critical Host Factor for Successful Malaria Liver Stage Development, Int. J. Parasitol 37: 483-489 (2007)

Non-patent Document 4: Kamijo A. et al., Urinary Liver-type Fatty Acid Binding Protein as a Useful Biomarker in Chronic Kidney Disease, J. Mol. Cell. Biochem. 284: 175-182 (2006)

SUMMARY OF THE INVENTION

The present invention was made in view of such circumstances heretofore, and an object of the invention is to provide a method for malaria testing which enables determination of the presence of malaria infection and the extent of the infection in a convenient manner; and a reagent or kit which can be used in the test method.

The present inventors carried out diligent research in order to solve the foregoing problems. Consequently, it was found that there is a correlation between malaria infection and the amount of the urinary L-FABP of a subject animal. Conventionally, it has been known that the amount of the L-FABP in blood is significantly increased in the case of liver disease, while the amount of the urinary L-FABP is not increased (Non-patent Document 4). In other words, an increase of the amount of the urinary L-FABP resulting from malaria infection is not relevant to the disclosure in Non-patent Document 3. Additionally, it is also reported in Non-patent Document 4 that the amount of the urinary L-FABP is significantly increased in the case of kidney disease. However, according to the studies performed by the present inventors, it was ascertained that renal dysfunction is not caused, even in the case of an infection with malaria leading to a significant increase in the amount of the urinary L-FABP. That is, it was newly found by the present inventors that there is a correlation between malaria infection and the amount of the urinary L-FABP of the subject animal. More specifically, the present invention provides the following.

The first aspect of the present invention provides a method for malaria testing including the step of detecting a L-FABP present in urine collected from a subject animal.

The method according to the first aspect may further includes the step of comparing the amount of the L-FABP present in the urine collected from the subject animal with a threshold.

The second aspect of the present invention provides a reagent or kit for testing, which can be used in the method according to the first aspect.

The reagent or kit according to the second aspect may includes an antibody that specifically binds to a L-FABP.

The present invention provides a method for malaria testing which enables testing for the presence of malaria infection and the extent of the infection in a convenient manner, and a reagent or kit which can be used in the method.

DETAILED DESCRIPTION OF THE INVENTION

<Method for Malaria Testing>

Figure 1:
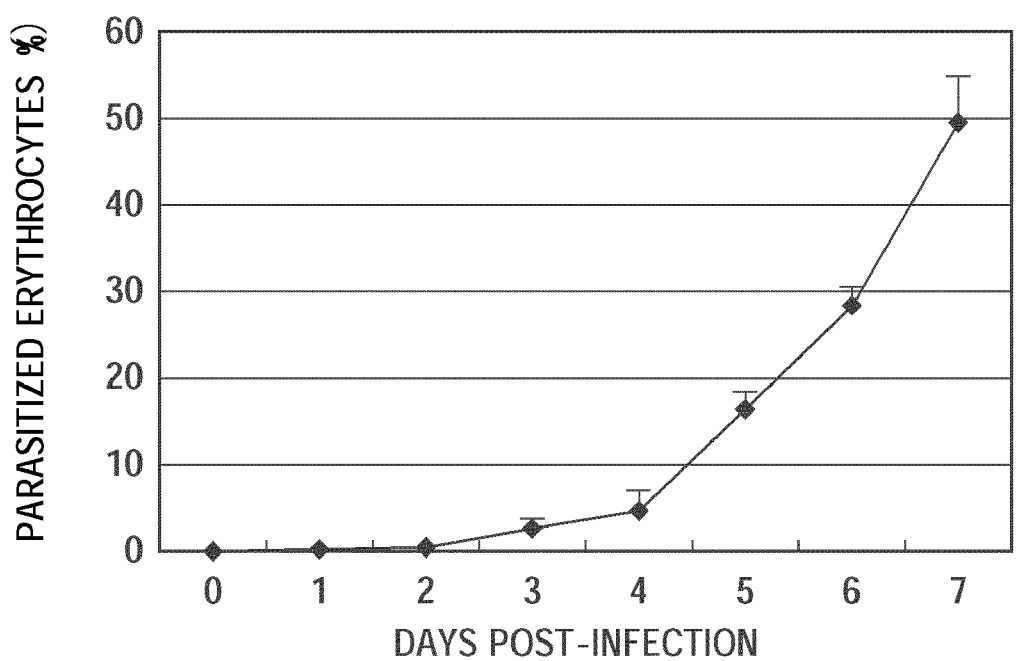
FIG. 1 shows a view illustrating the alteration of the rate of parasitized erythrocytes in peripheral blood in hL-FABP Tg mice following infection with a *P. berghei* ANKA strain.

The method for malaria testing according to the present invention includes the step of detecting a L-FABP present in urine collected from a subject animal.

The subject animal includes animals which can be infected with malaria, such as e.g., humans, monkeys, murines, birds and the like, and is preferably humans.

The detection of L-FABP present in urine is preferably carried out by immunochemical assay using an antibody that specifically binds thereto.

The antibody may be prepared by using L-FABP as an immunizing antigen. When a naturally occurring L-FABP is used as the immunizing antigen, L-FABP can be isolated from the liver, kidney and the like. The isolation thereof can be carried out according to the method disclosed in the literature (Kelvin et al., J. Biol. Chem. 263: 15762-15768 (1988)) as follows. The extirpated organ is homogenized, and subjected to ultra-centrifugation. The thus obtained cytoplasm fractions are separated by gel filtration, anion exchange chromatography or the like, and the fractions containing L-FABP are selected and isolated based on the molecular weight or fatty acid binding activity as indicators. Further, the fractions thus obtained are subjected to SDS-polyacrylamide gel electrophoresis for further purification or for confirmation that a single band is yielded. The amino acid composition or the amino acid sequence at the N-terminus of the purified protein is determined, and the results thereof are compared with the amino acid compositions or amino acid sequence as reported, by which the protein is confirmed to be a desired molecular species.

The fatty acid binding activity of L-FABP can be easily assayed, for example, by using a fluorescent probe such as ANS (1-anilinonaphthalene-8-sulfonic acid) (manufactured by Polysciences, Inc.). The fluorescent probe increases its fluorescent intensity by binding to a highly hydrophobic region such as the fatty acid binding site of L-FABP. For example, after ANS is added to a solution containing L-FABP and mixed, the fluorescence intensity (excitation wavelength: 372 nm; fluorescence wavelength: 480 nm) can be determined. In addition, the fatty acid binding activity of L-FABP can be also determined using RI-labeled fatty acid.

For reference, since L-FABP shows a high homology among humans, mice, pigs, cows and rats, and it is known that the homology is no less than 90% at the amino acid level, it is possible to utilize, for example, a mouse L-FABP as an antigen for obtaining an antibody that binds to human L-FABP. This case is advantageous in that the preparation of the antigen can be readily conducted.

The L-FABP used as an immunizing antigen may be a recombinant protein produced by a genetic engineering technique. Since the amino acid sequence and gene sequence of L-FABP have already been reported (Veerkamp and Maatman, Prog. Lipid Res. 34: 17-52 (1995)), a recombinant FABP can be prepared by a genetic engineering technique, for example, by designing a primer based on those reported data, cloning a cDNA from a suitable cDNA library by PCR, and using the cDNA thus obtained.

In addition, a fragment of L-FABP, or a synthesized peptide having a partial sequence thereof can be used as an immunizing antigen, if necessary, after combining with a carrier of a high molecular substance (bovine serum albumin, hemocyanin, etc.).

The antibody that specifically binds to L-FABP may be any of antiserum, polyclonal antibody, monoclonal antibody, and the like.

The antibody preferably has high specificity, and for example, one which substantially does not cross-react with the H-FABP is desired. In order to obtain an antibody having higher specificity, it is desirable to use a highly purified antigen.

In the preparation of the antibody, a warm-blooded animal is inoculated and immunized with a purified antigen prepared as described above. The immunized warm-blooded animal includes, for example, mammals (e.g., rabbits, sheep, rats, mice, guinea pigs, horses, pigs, etc.), and birds (e.g., chickens, ducks, geese, etc.). When a rabbit is immunized, for example, about 100 μg to 1 mg of the antigen is emulsified in a physiological saline solution and Freund's complete adjuvant (about 1 ml), and the resultant is subcutaneously injected into the back or the paw of the hind leg of the animal. After the initial inoculation, the adjuvant is changed to a Freund's incomplete adjuvant, and then the rabbit is inoculated and immunized with the antigen 3 to 8 times every 2 to 4 weeks. The antigen collected from the rabbit about 7 to 12 days after the final inoculation may be used. When a mouse is immunized, in general, the antigen at a dose of 10 to 30 μg/animal is inoculated for immunization subcutaneously, intraperitoneally or intravenously 3 to 8 times about every two weeks, and the antibody collected from the mouse about 2 to 4 days after the final inoculation may be used.

The polyclonal antibody can be prepared by collecting the blood from the animal thus immunized, separating the serum (antiserum), and then collecting IgG fractions therefrom. The polyclonal IgG can be obtained by collecting IgG fractions from the antiserum by affinity chromatography or the like using a Protein G column, for example.

The monoclonal antibody can be produced from hybridoma, which is obtained by fusing immortalized cells with antibody-producing cells collected from the inoculated animals. The immunized animal for the monoclonal antibody is preferably a mouse or a rat. The production of hybridoma may be carried out according to the method of Kohler & Milstein (Nature 256: 495-897 (1975)), as follows. More specifically, antigen-producing cells (spleen cells or lymph node cells, etc.) are collected from the animal immunized as mentioned above, and subjected to cell fusion with suitable immortalized cells. The immortalized cells are preferably a cell line of myeloma cells (NSI-Ag4/1, Sp2/O-Agl4, etc.). The myeloma cells are preferably non-secretors, which do not produce antibody or H-chain or L-chain of immunoglobulin, and have a selective marker, which can be used to distinguish the fused hybridoma from the non-fused myeloma cells in a selective medium. For example, cell lines having 8-azaguanine-resistance (hipoxanthine-guanine-phosphoribosyl transferase deficiency), thymidine kinase deficiency, etc. as a selective marker are often used.

The cell fusion is carried out by adding a suitable fusion promoter such as polyethylene glycol. The cell fusion is preferably carried out at a ratio of about 10 antibody-producing cells per one immortalized cell, and at a cell density of about $10^6$ cells/ml of the antibody-producing cells.

The fused cells are properly diluted, and incubated for 1 to 2 weeks in a selective medium. For example, when myeloma cells resistant to 8-azaguanine are used and cultured in a medium containing HAT (hypoxanthine, aminopterin, thymidine), non-fused myeloma cells die and non-fused antibody-producing cells also die because the cell division cycle is restricted, but only fused cells can keep division and survive in a selective medium.

After cultivation in a selective medium, the presence of the desired antibody is detected, for example, by carrying out an enzyme immunoassay for the culture supernatant thereof, followed by subjecting to cloning with a limiting dilution method, by which the desired hybridoma capable of producing a monoclonal antibody that recognizes the desired antigen can be selected. The selection of hybridoma is carried out so as to select a hybridoma (monoclonal antibody) having preferable properties in terms of antibody titer, class or subclass of antibody, affinity for antigen, specificity, epitope, etc. The IgG class of a monoclonal antibody is preferable.

The monoclonal antibody-producing hybridoma is implanted, for example, into the peritoneal of the animal used in immunization, and after a certain time period, ascites is collected therefrom. The desired monoclonal antibody can be isolated from the ascites thus obtained. Alternatively, the hybridoma is cultured in a suitable medium for animal cell culture, and the desired monoclonal antibody may be isolated from the culture medium. Besides, when the desired hybridoma is isolated, then a gene encoding the desired monoclonal antibody is obtained therefrom, and the desired monoclonal antibody can be expressed and produced in a suitable host by a conventional gene recombinant technique.

The purification-isolation of the antibody is carried out by a conventional purification method, such as ammonium sulfate precipitation, gel chromatography, ion exchange chromatography, or affinity chromatography, which may be employed in combination, as needed.

Using the antibody thus obtained, L-FABP (antigen) present in urine can be detected and quantitatively determined by an immunochemical assay.

The detection and quantitative determination may be carried out by utilizing a conventional method such as enzyme immunoassay (EIA), chemiluminescent immunoassay, etc. Also, a method such as radioimmunoassay (RIA) or fluoroimmunoassay may be utilized if desired. Specifically, a competitive method using an antibody and labeled antigen, a sandwich EIA using a combination of two kinds of monoclonal antibodies or polyclonal antibodies (or a combination of a monoclonal antibody and a polyclonal antibody) having a distinct recognition site for the antigen, etc. can be given as examples. In these assays, an antigen or an antibody may be immobilized on a suitable carrier such as gel particles, cellulose particles, polyacrylamide gel, a physical absorbent (e.g., glass, styrene resin), if necessary. For example, a solid phase method is frequently utilized in which an antigen or an antibody is adsorbed onto a solid phase such as polystyrene plate or beads. Further, a Western Blotting method may be applied for detection.

In the above mentioned immunochemical assays, a labeled antigen or a labeled antibody may be used, if necessary. The labeling is carried out using radioisotopes (e.g., $^{124}I$, $^{14}C$, $^{3}H$), fluorescence substances (e.g., fluorescein isothiocyanate, etc.) and the like, in addition to enzymes (e.g., peroxidase, alkaline phosphatase, etc.), and luminescent substances (e.g., acridinium ester, isoluminol, luciferin, etc.). Besides, a method using a combination of biotin labeling and streptoavidin may also be utilized.

By detection and quantitative determination of L-FABP present in the test sample as in the foregoing, the presence of malaria infection as well as the extent of the infection can be conveniently determined. More specifically, malaria infection is determined when the amount of the L-FABP present in urine is greater than a specified threshold, and a higher extent of the infection is determined as the amount becomes greater. This specified threshold may be predetermined, for example, based on the average value in urine collected from control animals not infected with malaria.

In addition, therapeutic effects with a medical agent, and the like can be also determined by collecting urine from a subject animal infected with malaria several times at different time points, and determining the time-dependent alteration of the amount of L-FABP.

<Reagent or Kit for Testing>

The reagent or kit for testing according to the present invention is used for the test method described above. Examples of the reagent for testing include anti-L-FABP antibodies, labeled products thereof, and the like. The labeled antibody includes, for example, an antibody conjugated with an enzyme such as peroxidase (enzyme-labeled antibody), a biotinylated antibody (biotin-labeled antibody), etc. The kit for testing is, for example, one in which an anti-L-FABP antibody is absorbed or bound onto a carrier such as beads or a plate (96-well microplate, etc.). In this case, the kit for testing may further contain other reagents necessary for EIA, etc., for example, enzyme-labeled secondary antibody, and a coloring substrate, etc. Additionally, a gold colloid immunoassay may also be utilized as in commercially available pregnancy test kits.

EXAMPLES

Hereinafter, the present invention is explained in detail by way of Examples, but the present invention should not in any way be construed to be limited by the following description.

Example 1

Production of Transgenic Mouse into which Human L-FABP Gene is Introduced (hL-FABP-Tg mouse)

In order to produce transgenic mice into which a human L-FABP gene is introduced (hL-FABP-Tg mouse), male BCF1 mice no younger than 13 weeks old for infertile mating and natural mating, female ICR mice no younger than 10 weeks old for embryo transplantation and foster parent, male BDF1 mice no younger than 13 weeks old for mating, and female BDF1 mice no younger than 8 weeks old for ovum collection were used, respectively. Thus obtained transgenic mice (B6C3F1) were back crossed with BALB/cA mice to produce hL-FABP-Tg mice.

Example 2

Amount of Urinary hL-FABP Excreted by hL-FABP-Tg Mouse Infected with P. berghei ANKA Strain The P. berghei ANKA strain causes fatal infection in Balb/cA mice. In experimental infection, an intraerythrocytic protozoan parasite of P. berghei ANKA strain was used, and the hL-FABP-Tg mice (n=3) produced in Example 1 were used as subject animals. Additionally, in order to prevent influence by passive immunity, a Balb/cA RAG-2 knock out mouse was infected with the protozoan parasite of P. berghei ANKA strain, and used as a donor of parasitized erythrocytes for use in the experiment.

The hL-FABP-Tg mouse was intraperitoneally infected with $1 \times 10^6$ cells of parasitized fresh erythrocytes obtained from the infected RAG-2 knock out mouse. Following infection, the rate of parasitized erythrocytes in peripheral blood in the hL-FABP-Tg mouse was determined with Giemsa-stained blood smear preparations. The results are shown in FIG. 1.

Figure 2A:
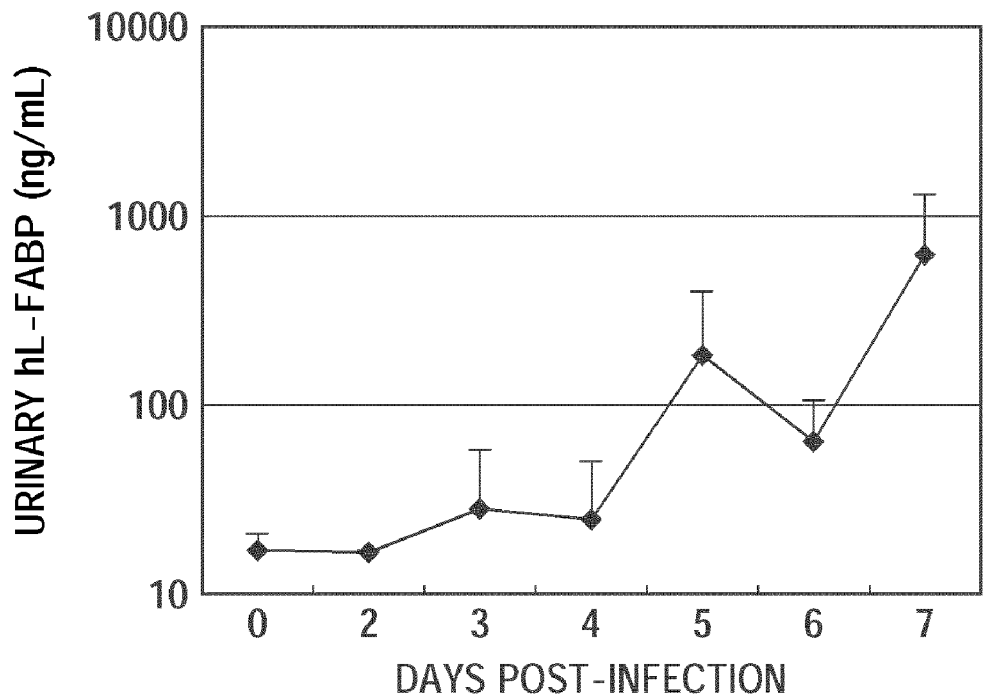
FIG. 2A and FIG. 2B show a view illustrating the alteration of the amount of urinary hL-FABP excreted by hL-FABP Tg mice following infection with a *P. berghei* ANKA strain.
Figure 2B:
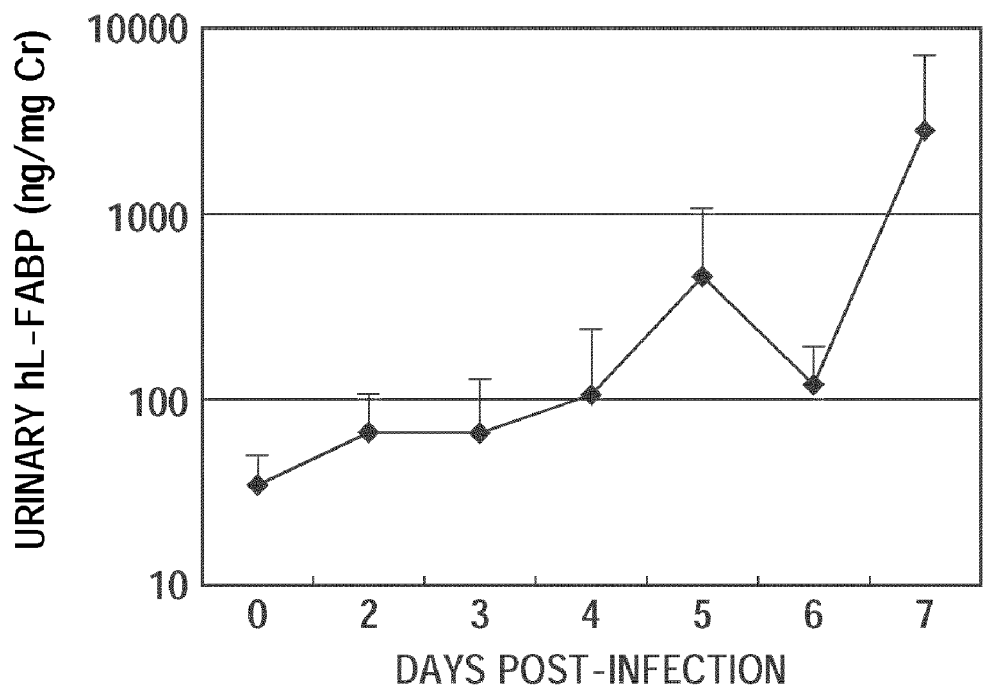

In addition, spot urine was collected every day by spontaneous urination. The amount of the excreted urinary hL-FABP was determined by ELISA (hL-FABP measuring kit, manufactured by IBL Co., Ltd.). Thus measured values are shown in FIG. 2A, and the values derived by correcting with the amount of creatinine are shown in FIG. 2B.

As seen from FIG. 1, the rate of parasitized erythrocytes in peripheral blood following the infection with the P. berghei ANKA strain was 0.37% (SE: ±0.033) on day 2 post-infection. Thereafter, the rate of parasitized erythrocytes in peripheral blood rapidly increased, and reached 49.43% (SE: ±3.068) on day 7 post-infection. On the other hand, as seen from FIG. 2A, the amount of urinary hL-FABP in the hL-FABP-Tg mouse increased as the infection progressed from 17 ng/mL (SE: ±2.367) before infection with the P. berghei ANKA strain, and reached 187 ng/mL (SE: ±127.074) on day 5 post-infection and 631 ng/mL (SE: ±380.531) on day 7 post-infection. Also in the graph drawn with values corrected with creatinine, a similar tendency is shown (FIG. 2B).

As is seen from these results, the increase in the amount of the excreted urinary hL-FABP was consistent with the increase in the rate of parasitized erythrocytes in peripheral blood. Therefore, it is believed that detection of hL-FABP in urine enables infection with malaria to be detected, and that measurement of the amount of excretion of hL-FABP enables the degree of progression of malaria to be determined.

Example 3

Histopathological Analysis of Kidney in hL-FABP-Tg Mouse on Day 7 Following Infection with P. berghei ANKA Strain The hL-FABP-Tg mouse on day 7 following infection with the P. berghei ANKA strain used in Example 2 was dissected for inspection, and histopathological analysis of the kidney was carried out by PAS staining. As a control, a hL-FABP-Tg mouse administered with cisplatin was used (Negishi K. et al., Kidney Int. 73 (12): 1374-1384(2008)). With respect to this control mouse, after a male 8- to 10-week old hL-FABP-Tg mouse was preliminarily fed for one week, 20 mg/kg of cisplatin dissolved in physiological saline (total solution: 60 mL/kg) was intraperitoneally administered once, and the mouse was dissected for inspection 72 hours later to carry out a histopathological analysis of the kidney by PAS staining. This control mouse exhibited an amount of hL-FABP excreted into urine of a similar level to the amount of excretion from the hL-FABP-Tg mouse on day 7 following infection with the P. berghei ANKA strain. The results obtained with the hL-FABP-Tg mouse infected with the P. berghei ANKA strain are shown in FIG. 3A, while the results obtained with the control mouse administered with cisplatin are shown in FIG. 3B.

Figure 3A:
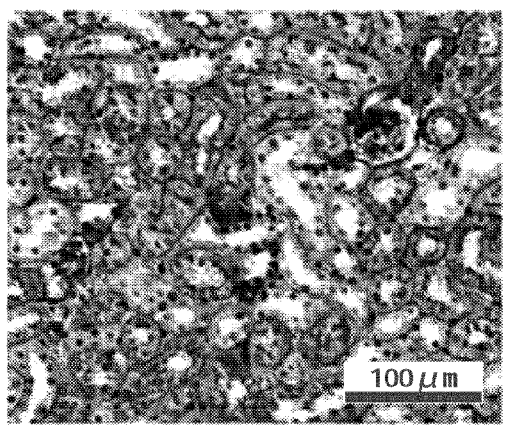
FIG. 3A shows a view illustrating a renal tissue section of a hL-FABP Tg mouse on day 7 following infection with a *P. berghei* ANKA strain.
Figure 3B:
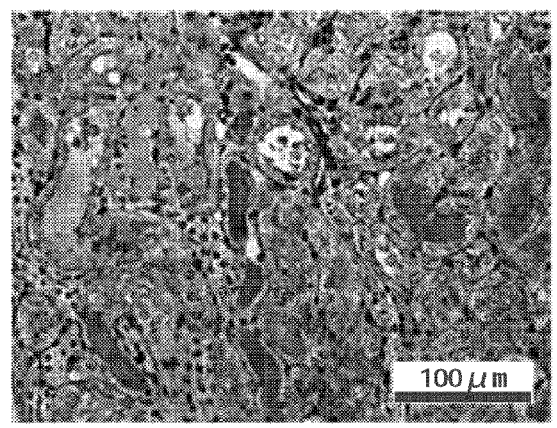
FIG. 3B shows a view illustrating a renal tissue section of a hL-FABP Tg mouse post administration with cisplatin.

As seen from FIG. 3A and FIG. 3B, marked acute kidney tubular necrosis such as necrosis and detachment of renal tubular epithelium, disappearance of brush border, and enlargement of renal tubular lumen developed in the control mouse administered with cisplatin (FIG. 3B), although obviously a lesser extent of the tissue impairment was found in the hL-FABP-Tg mouse on day 7 following infection with the *P. berghei* ANKA strain, as compared with the control mouse that exhibited a similar level of excretion of hL-FABP into urine (FIG. 3A). These results suggest that the increase in the amount of the excreted urinary hL-FABP resulting from malaria infection was caused by a mechanism different from that in renal dysfunction.

Example 4

Amount of Urinary hL-FABP Excreted by hL-FABP-Tg Mouse Infected with *P. chabaudi*

*P. chabaudi* is not fatal to Balb/cA mice; parasitaemia develops, followed by resistance to infection. In experimental infection, a *P. chabaudi* intraerythrocytic protozoan parasite was used, and the hL-FABP-Tg mice (n=10; Tg-1 to Tg-10) produced in Example 1 were used as subject animals. Additionally, in order to prevent influence by passive immunity, a Balb/cA RAG-2 knock out mouse was infected with the *P. chabaudi* protozoan parasite, and used as a donor of parasitized erythrocytes for use in the experiment.

The hL-FABP-Tg mouse was intraperitoneally infected with $1 \times 10^5$ cells of parasitized fresh erythrocytes obtained from the infected RAG-2 knock out mouse. Following infection, the rate of parasitized erythrocytes in peripheral blood in the hL-FABP-Tg mouse was determined with Giemsa-stained blood smear preparations. The results are shown in FIG. 4.

In addition, pooled urine was collected with a metabolism cage. The amount of the excreted urinary hL-FABP was determined by ELISA (hL-FABP measuring kit, manufactured by IBL Co., Ltd.). The measured values are shown in FIG. 5A, and the values derived by correcting with the amount of creatinine are shown in FIG. 5B.

Figure 4:
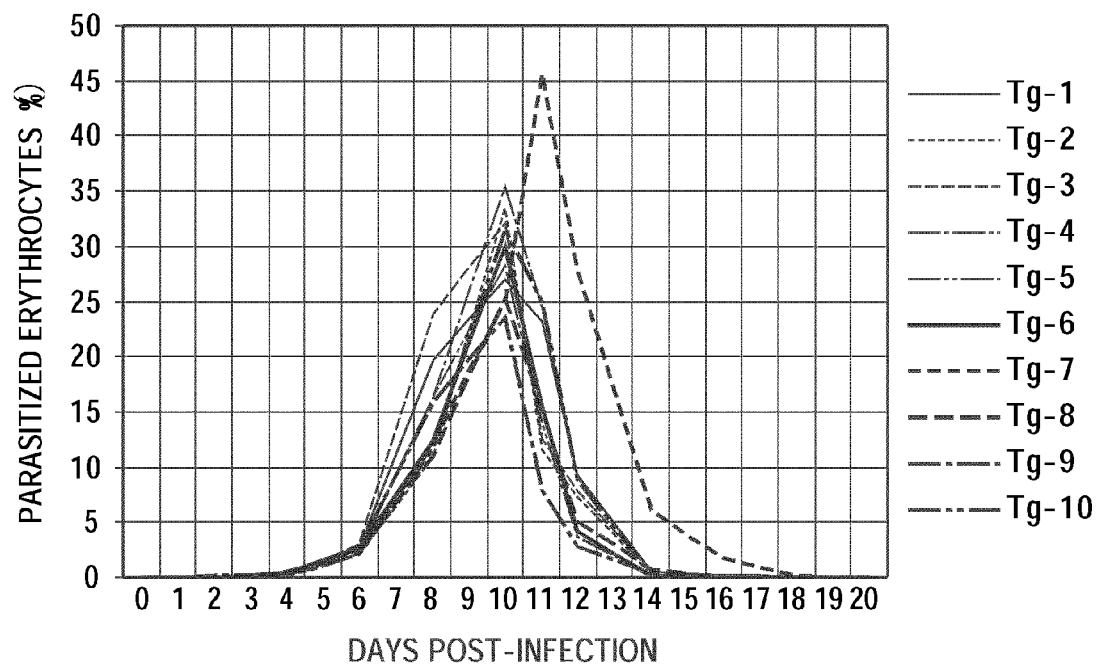
FIG. 4 shows a view illustrating the alteration of the rate of parasitized erythrocytes in peripheral blood in hL-FABP Tg mice following infection with *P. chabaudi;*

As seen from FIG. 4, the rate of parasitized erythrocytes in peripheral blood following the infection with *P. chabaudi* was 0.26% (SE: ±0.036) on day 4 post-infection. Thereafter, the rate of parasitized erythrocytes in peripheral blood rapidly increased, and the highest rate of 29.1% (SE: ±1.246) was shown on day 10 post-infection. Subsequently, the rate of parasitized erythrocytes in peripheral blood started to decline, and was 8.58% (SE: ±2.261) on day 12 post-infection and 0.9% (SE: ±0.582) on day 14 post-infection, and reached 0% on day 20 post-infection.

Figure 5A:
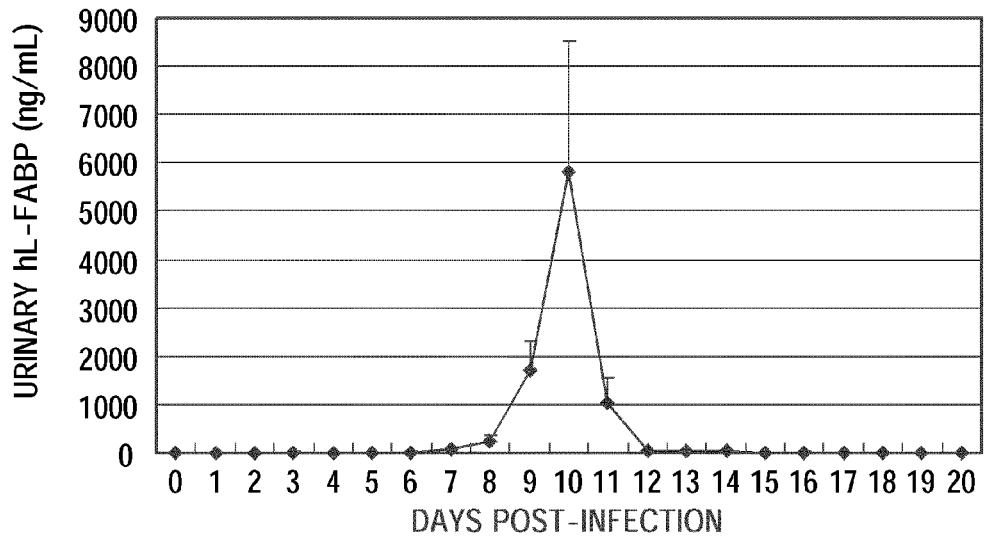
FIG. 5A and FIG. 5B show a view illustrating the alteration of the amount of urinary hL-FABP excreted by hL-FABP Tg mice following infection with *P. chabaudi;*
Figure 5B:
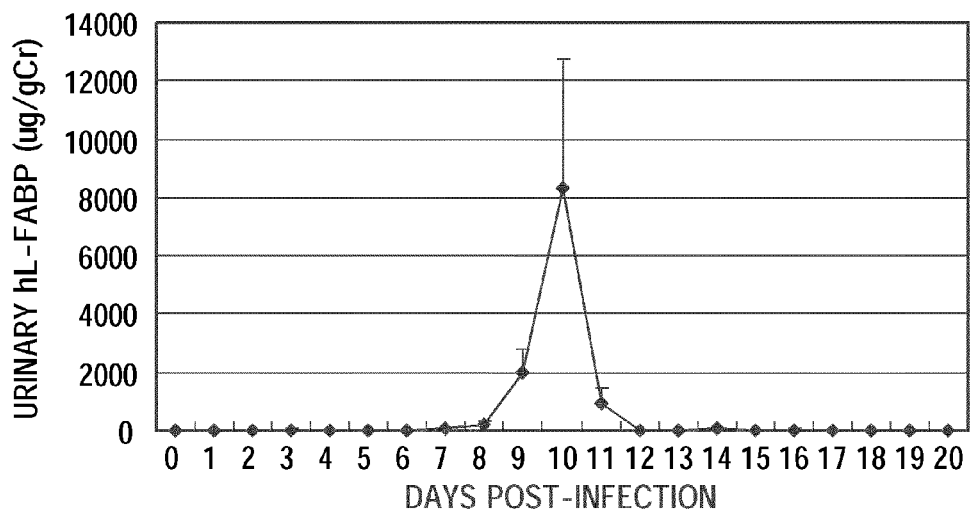

On the other hand, as seen from FIG. 5A, the amount of urinary hL-FABP in the hL-FABP-Tg mouse increased as the infection progressed from 5.9 ng/mL (SE: ±1.9) before infection with *P. chabaudi*, and exhibited the highest value of 5801.6 ng/mL (SE: ±2715.6) on day 10 post-infection. Subsequently, the amount of the excreted urinary hL-FABP started to decline, and was 26.3 ng/mL (SE: ±4.0) on day 12 post-infection and 24.7 ng/mL (SE: ±7.7) on day 14 post-infection, and reached 4.8 ng/mL (SE: ±1.6) on day 20 post-infection. Also in the graph plotted with values corrected with creatinine, a similar tendency is shown (FIG. 5B).

As is seen from these results, the increase and decrease in the amount of the excreted urinary hL-FABP was consistent with the increase and decrease in the rate of parasitized erythrocytes in peripheral blood. Accordingly, it is believed that the amount of the excreted urinary hL-FABP can be a useful biomarker for deciding the course following the treatment since it quickly reflects disappearance of the protozoan in peripheral blood.

Example 5

Alteration of the Amount of Urinary hL-FABP excreted by hL-FABP-Tg Mouse Infected with *P. berghei* ANKA Strain, by Treatment with Chloroquine In experimental infection, the intraerythrocytic protozoan parasite of the *P. berghei* ANKA strain was used, and the hL-FABP-Tg mice (n=4) produced in Example 1 were used as subject animals. Additionally, in order to prevent influence by passive immunity, a Balb/cA RAG-2 knock out mouse was infected with the protozoan parasite of *P. berghei* ANKA strain, and used as a donor of parasitized erythrocytes for use in the experiment.

Figure 6:
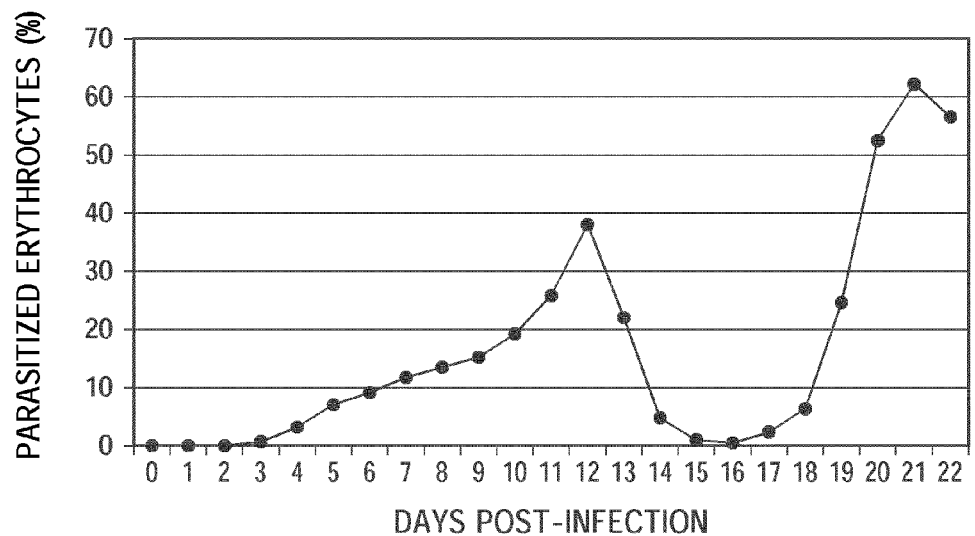
FIG. 6 shows a view illustrating the alteration of the rate of parasitized erythrocytes in peripheral blood in hL-FABP-Tg mice following infection with a *P. berghei* ANKA strain, by a chloroquine treatment.

The hL-FABP-Tg mouse was intraperitoneally infected with $1 \times 10^6$ cells of parasitized fresh erythrocytes obtained from the infected RAG-2 knock out mouse. Thereafter, on day 12, day 13, and day 14 following the infection, chloroquine dissolved in physiological saline was intraperitoneally administered every day for the treatment of malaria, with 15 mg/kg on day 1 of the treatment, and 5 mg/kg on day 2 and day 3. On the other hand, the rate of parasitized erythrocytes in peripheral blood in the hL-FABP-Tg mouse was determined every day with Giemsa-stained blood smear preparations until day 22 post-infection. The results are shown in FIG. 6. Furthermore, pooled urine was collected with a metabolism cage, and the amount of the excreted urinary hL-FABP was determined by ELISA (hL-FABP measuring kit, manufactured by IBL Co., Ltd.). The amounts of the excreted urinary hL-FABP derived by correcting with the amount of creatinine are shown in FIG. 7.

As seen from FIG. 6, the rate of parasitized erythrocytes in peripheral blood following infection with the *P. berghei* ANKA strain gradually increased, and the highest rate of 37.8% was shown on day 12 post-infection. The rate of parasitized erythrocytes in peripheral blood started to decline upon the treatment with chloroquine, and reached 4.9% on day 14 post-infection, and 1.1% on day 15 post-infection. When the treatment with chloroquine was stopped, the rate of parasitized erythrocytes in peripheral blood increased again, and elevated to 6.3% on day 18 post-infection and to 24.6% on day 19 post-infection.

Figure 7:
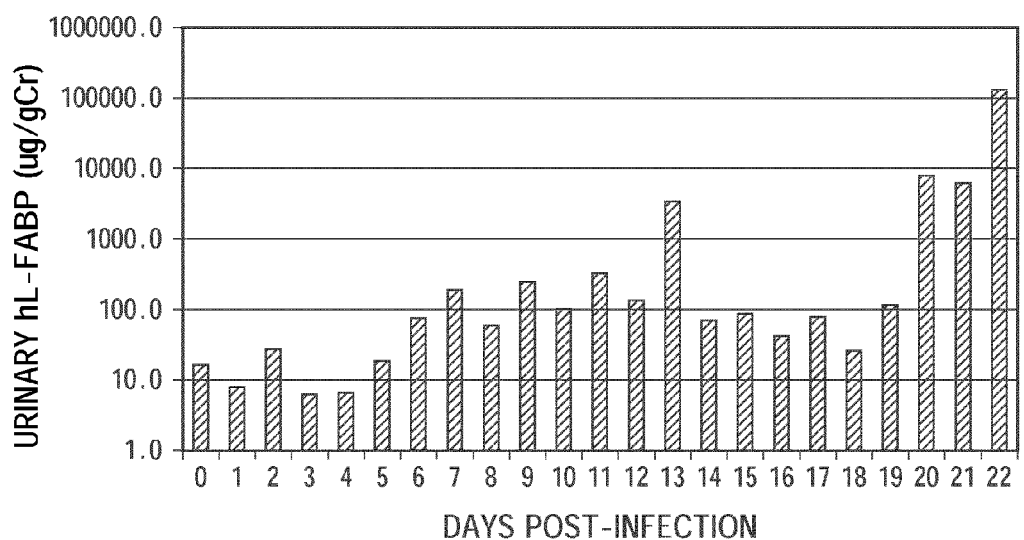
FIG. 7 shows a view illustrating the alteration of the amount of urinary hL-FABP excreted by hL-FABP-Tg mice following infection with a *P. berghei* ANKA strain, by a chloroquine treatment.

On the other hand, as seen from FIG. 7, the amount of urinary hL-FABP in the hL-FABP-Tg mouse increased as the infection progresses from 16 μg/g Cr before infection with the *P. berghei* ANKA strain, and exhibited the highest value of 3454 μg/g Cr on day 13 post-infection. The amount of the excreted urinary hL-FABP rapidly decreased upon the treatment with chloroquine, and reached 85 μg/g Cr on day 15 post-infection, and 43 μg/g Cr on day 16 post-infection. When the treatment with chloroquine was stopped, the amount of the excreted urinary hL-FABP increased again along with the recurrence of malaria, and elevated to 113 μg/g Cr on day 19 post-infection, and to 8,013 μg/g Cr on day 20 post-infection.

As seen from these results, the amount of the excreted urinary hL-FABP decreased along with the treatment with chloroquine and increased with the recurrence of malaria, and further, the increase and decrease thereof were consistent with those in the rate of parasitized erythrocytes in peripheral blood. Therefore, it is believed that the amount of the excreted urinary hL-FABP can be a useful biomarker for determining the effect of malaria therapy.

Example 6

Amount of Urinary hL-FABP Excreted by Malaria Infected Patient

For malaria infected patients who received definite diagnosis of malaria infection (four cases) and a patient with fever but not infected with malaria (one case) as subjects, the serum creatinine, CRP and body temperature were determined for each subject.

In addition, the amount of urinary hL-FABP excreted by each subject was determined as follows. Quantitative determination was carried out on the urine collected from each subject with a kit for measurement of urinary hL-FABP (manufactured by CMIC Co., Ltd.) by a sandwich ELISA method in which two kinds of monoclonal antibodies to hL-FABP are used. More specifically, an equal volume, i.e., 50 μL of the urine sample, and 50 μL of a pretreatment liquid were mixed for 10 min, and 20 μL of aliquot was added to a coating plate of the primary antibody, to which 100 μL of a reaction buffer was added beforehand, followed by mixing. After leaving to stand still for 1 hour, the plate was washed, and an enzyme-labeled secondary antibody was added thereto to allow the reaction to proceed for an additional 1 hour. After washing again, the addition of the enzyme substrate provided coloring corresponding to the amount of the antigen within 30 minutes. The resulting color was employed for quantitative determination with an absorptiometer.

Moreover, urinary hL-FABP was measured on the urine from the same subject by the Dip-test (manufactured by CMIC Co., Ltd.). The Dip-test utilizes a principle according to an immunochromatographic method in which an anti-hL-FABP monoclonal antibody bound to gold colloid is used to yield a band corresponding to the amount of the antigen on a test line, thereby enabling visualization. The intensity of the bands was qualitatively evaluated by scoring from 0 (=negative) to 3 (=strongly positive).

The age, sex (male (M)/female (F)), the execution of malaria treatment, serum creatinine (mg/dL), CRP (mg/dL), body temperature (° C.), the amount of the excreted urinary hL-FABP (ng/mL), and the Dip-test score of each subject are shown in Table 1 below. For reference, the average value of the amount of the excreted urinary hL-FABP measured on 97 cases for healthy persons not infected with malaria (26 cases: male, 71 cases: female, average age: 33 years old) was 6.5 ng/mL (Kamijo A. et al., J. Lab. Clin. Med. 143(1): 23-30 (2004)).

malaria. These malaria infected patients exhibited normal levels for both the serum creatinine and CRP. Thus, it is believed that the higher value of the amount of the excreted urinary hL-FABP is less likely to result from renal diseases and inflammatory diseases. In particular, the untreated patient with high fever and infected with malaria (40-year old male) exhibited an extremely high value of the amount of excreted urinary hL-FABP. In contrast, the patient with fever but not infected with malaria (50-year old male, renal function: normal, CRP: abnormal) exhibited an amount of the excreted urinary hL-FABP falling within a normal range. Since the elevation of body temperature via the thermoregulatory center accompanies an increase in malaria-parasitized erythrocytes in peripheral blood, the possibility of specific correlation is suggested between the amount of the excreted urinary hL-FABP, and the severity of fever in patients infected with malaria, but not in patients not infected with malaria.

Moreover, the score of the dip-test correlated with the amount of the excreted urinary hL-FABP. This suggests the possibility of determining the severity of a malaria infection using the Dip-test, which is a simplified kit, within a short period of time in a convenient manner.

What is claimed is:

1. A method for identifying the presence and/or severity of erythrocyte stage malaria disease in a subject animal, comprising:

obtaining a sample of urine from the subject animal;

contacting the urine sample from the subject animal with an antibody to a liver-type fatty acid binding protein (L-FABP), wherein the antibody binds to L-FABP present in the urine;

detecting binding of the antibody and the L-FABP in the urine sample; and quantifying the amount of antibody bound to L-FABP present in the urine sample, wherein the presence of an amount of antibody bound to L-FABP in an amount greater than an average amount of L-FABP present in urine from control animals not infected with malaria indicates the presence of erythrocyte malaria in the subject animal.

2. The method of claim 1, wherein said animal is a human.

3. The method of claim 1, wherein said antibody is a polyclonal antibody.

4. The method of claim 1, wherein said antibody is a monoclonal antibody.

TABLE 1

| Age | Sex | Treatment | Serum creatinine (mg/dL) | CRP (mg/dL) | Body temperature (° C.) | Urinary hL-FABP (ng/mL) | Dip-test score |
|---|---|---|---|---|---|---|---|
| 19 | M | Medicated | 0.72 | 0.6 | 37.0 | 9.8 | 1 |
| 35 | F | Medicated | 0.82 | <0.6 | 37.1 | 10.4 | 1 |
| 18 | M | Untreated | 0.77 | <0.6 | 37.3 | 45.5 | 1 |
| 40 | M | Untreated | 0.86 | <0.6 | 39.4 | 272.9 | 3 |
| 50 | M | No malaria | 0.76 | 4.1 | 38.7 | 0.6 | 0 |

As is clear from Table 1, all of the malaria infected patients exhibited increased amounts of excreted urinary hL-FABP compared with the patient with fever but not infected with 5. The method of claim 1, wherein said detecting and/or quantifying are performed by a method selected from the group consisting of an enzyme immunoassay, a chemiluminescent immunoassay, a radioimmunoassay a fluoroimmunoassay and a gold colloid immunoassay.

6. The method of claim 1, wherein said L-FABP or antibody is immobilized on a solid phase.

7. The method of claim 1, wherein said antibody is labeled.

8. The method of claim 7, wherein said label is radiolabel, fluorescent label or enzyme label.

9. The method of claim 1, further comprising correlating a greater amount of antibody bound to L-FABP with a greater extent of infection with malaria.

* * * * *

UNITED STATES PATENT AND TRADEMARK OFFICE
CERTIFICATE OF CORRECTION

| | | |
|---|---|---|
| PATENT NO. | : 8,034,551 B2 | |
| APPLICATION NO. | : 12/405060 | |
| DATED | : October 11, 2011 | |
| INVENTOR(S) | : Takeshi Sugaya, Eisei Noiri and Yoshitsugu Matsumoto | |

It is certified that error appears in the above-identified patent and that said Letters Patent is hereby corrected as shown below:

Title page, [Item 56], Under Other Publications, Change "cisplati" to --cisplatin--.

Col. 5, Line 54, Change "Agl4," to --Ag14,--.

Col. 5, Line 60, Change "(hipoxanthine" to --(hypoxanthine--.

Col. 6, Lines 66-67, Change "streptoavidin" to --streptavidin--.

Col. 12, Line 44, In Claim 1, after "erythrocyte" insert --stage--.

Col. 13, Lines 1-2, In Claim 5, change "chemiluninescent" to --chemiluminescent--.

Signed and Sealed this
Nineteenth Day of June, 2012

David J. Kappos
*Director of the United States Patent and Trademark Office*